United States Patent
Kim et al.

(10) Patent No.: US 8,625,618 B2
(45) Date of Patent: Jan. 7, 2014

(54) HEALTH CARE SYSTEM, AND APPARATUS AND METHOD FOR CONTROLLING HEALTH CARE

(75) Inventors: Seok Chan Kim, Seoul (KR); Kunsoo Shin, Seongnamsi-si (KR); Gunguk Park, Suwon-si (KR); Jong Pal Kim, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 186 days.

(21) Appl. No.: 13/192,616

(22) Filed: Jul. 28, 2011

(65) Prior Publication Data
US 2012/0184822 A1    Jul. 19, 2012

(30) Foreign Application Priority Data

Jan. 18, 2011    (KR) .......................... 10-2011-0005007

(51) Int. Cl.
*H04J 1/16*    (2006.01)
(52) U.S. Cl.
USPC ............ 370/401; 370/252; 370/329; 370/386
(58) Field of Classification Search
USPC .................................. 370/252, 329, 401, 386
See application file for complete search history.

(56) References Cited

U.S. PATENT DOCUMENTS

| | | | |
|---|---|---|---|
| 2002/0082480 A1* | 6/2002 | Riff et al. ...................... | 600/300 |
| 2006/0154642 A1 | 7/2006 | Scannell, Jr. | |
| 2009/0105566 A1 | 4/2009 | Smith et al. | |
| 2012/0023193 A1* | 1/2012 | Eisner et al. .................. | 709/217 |
| 2012/0108917 A1* | 5/2012 | Libbus et al. ................. | 600/301 |

FOREIGN PATENT DOCUMENTS

| | | |
|---|---|---|
| JP | 2005-124205 | 5/2005 |
| JP | 2006-060412 | 3/2006 |
| KR | 100762443 | 9/2007 |
| KR | 100782905 | 11/2007 |

\* cited by examiner

*Primary Examiner* — John Pezzlo
(74) *Attorney, Agent, or Firm* — NSIP Law

(57) ABSTRACT

An apparatus for controlling health care in a health care system is provided. The apparatus for controlling health care in a health care system includes a communication unit configured to transmit and/or receive a sensed biological signal, a determination unit configured to determine whether the health care system comprises, in addition to a first gateway through which the sensed biological signal is transmitted and/or received, at least one second gateway through which the sensed biological signal can be transmitted and/or received, and determine which gateway the sensed biological signal is to be transmitted and/or received through in response to the health care system comprising the second gateway, and a communication control unit configured to control a transmitting and/or receiving function of each gateway according to a result of the determining.

23 Claims, 8 Drawing Sheets

HEALTH CARE SYSTEM, AND APPARATUS AND METHOD FOR CONTROLLING HEALTH CARE

CROSS-REFERENCE TO RELATED APPLICATIONS

This application claims the benefit of Korean Patent Application No. 10-2011-0005007, filed on Jan. 18, 2011, in the Korean Intellectual Property Office, the entire disclosure of which is incorporated herein by reference for all purposes.

BACKGROUND

1. Field

The following description relates to a health care system and apparatus and method for controlling health care.

2. Description of the Related Art

U-Health Care, which has appeared in correspondence with development of communications technology, is a health management service utilizing a ubiquitous telemedicine technology. U-Health Care, which is short for ubiquitous health care, allows a user to be provided medical services without time or space constraints. U-Health Care provides medical services, in other words, health care, to a user based on a mobile device such as a mobile phone connected to a wireless network. U-Health Care also provides health care to a user based on any of other consumer electronics such as a computer connected to the Internet via a wired/wireless network, a television, or a combination thereof. Users may receive medical treatment anytime and anywhere from medical professionals based on information regarding health care provided through a mobile device or other consumer electronics.

In general, health care is provided from an independent health care system in which different devices exist, and is not provided from a health care system in which different devices may be converged.

SUMMARY

Provided is an apparatus and method for controlling a biological signal transmitting and/or receiving function of various gateways and a health care system.

Additional aspects will be set forth in part in the following description and, in part, will be understood from the description, or may be learned by practice of the presented examples. In one general aspect, an apparatus for controlling health care in a health care system is provided. The apparatus includes a communication unit configured to transmit and/or receive a sensed biological signal, a determination unit configured to determine whether the health care system comprises, in addition to a first gateway through which the sensed biological signal is transmitted and/or received, at least one second gateway through which the sensed biological signal can be transmitted and/or received, and determine which gateway the sensed biological signal is to be transmitted and/or received through in response to the health care system comprising the second gateway, and a communication control unit configured to control a transmitting and/or receiving function of each gateway according to a result of the determining.

In response to the determination unit determining that the health care system comprises the second gateway, the determination unit may determine the gateway to transmit and/or receive the sensed biological signal based on a user's setting, processing capacities of the gateways, or a combination thereof.

In response to the determination unit determining that the health care system comprises the second gateway, the communication control unit may control the transmitting and/or receiving function of the first gateway to be deactivated.

At least one of the gateways may further include a signal strength measurement unit for measuring a signal strength corresponding to a sensing unit for sensing a biological signal.

The health care controller may be included in a health care server.

The determination unit may determine whether a biological signal received from the first gateway via the communication unit is the same as a biological signal received from the second gateway. The communication control unit may control the gateways by generating a control signal for controlling the transmitting and/or receiving function of each gateway according to a result of the determining.

In response to the determination unit determining that the received biological signals are the same, the communication control unit may generate a control signal that requests that the transmitting and/or receiving function of the first gateway be deactivated.

In response to the measured signal strength being less than a threshold value or in response to the communication unit not receiving a biological signal from the second gateway, the communication control unit may generate a control signal that requests the transmitting and/or receiving function of the first gateway be activated.

The health care controller may be included in each gateway.

In response to the determination unit determining that the health care system comprises the second gateway, the communication unit comprised in the second gateway may transmit a control signal that requests the transmitting and/or receiving function of the first gateway be deactivated.

In response to the measured signal strength being less than the threshold value, the communication unit comprised in the second gateway may transmit a control signal that requests the transmitting and/or receiving function of the first gateway be activated.

The health care controller may be comprised in the sensing unit.

The biological signal may be either an electrocardiogram (ECG) signal or an electromyogram (EMG) signal.

In another aspect, a method of controlling health care in a health care system is provided. The method includes transmitting and/or receiving a sensed biological signal, determining whether the health care system comprises, in addition to a first gateway through which the sensed biological signal is transmitted and/or received, at least one second gateway through which the sensed biological signal can be transmitted and/or received, and determining which gateway the sensed biological signal is to be transmitted and/or received through in response to the health care system comprising the second gateway, and controlling a transmitting and/or receiving function of each gateway according to a result of the determining.

In response to a determination determining that the health care system comprises the second gateway, the determining may include determining the gateway to transmit and/or receive the sensed biological signal based on a user's setting, processing capacities of the gateways, or a combination thereof.

In response to a determination determining that the health care system comprises the second gateway, the controlling may include controlling the transmitting and/or receiving function of the first gateway to be deactivated.

At least one of the gateways may measure a signal strength corresponding to a sensing unit for sensing a biological signal.

A health care controller configured to perform the method of controlling health care being comprised in a health care server, the gateways, the sensing unit, or a combination thereof.

In response to the health care controller being comprised in the health care server, the determining may include determining whether a biological signal received from the first gateway is the same as a biological signal received from the second gateway, and the controlling may include controlling the gateways by generating a control signal for controlling the transmitting and/or receiving function of each gateway according to a result of the determining.

In response to a determination determining that the received biological signals are the same, the controlling may include controlling by generating a control signal that requests the transmitting and/or receiving function of the first gateway be deactivated.

In response to the measured signal strength being less than a threshold value or in response to the health care server not receiving a biological signal from the second gateway, the controlling may include controlling a control signal that requests the transmitting and/or receiving function of the first gateway be activated.

In response to the health care controller being comprised in each gateway, in response to a determination determining that the health care system comprises the second gateway, further comprising transmitting a control signal that may request the transmitting and/or receiving function of the first gateway be deactivated.

In response to the health care controller being comprised in each gateway, in response to the measured signal strength being less than a threshold value, further comprising transmitting a control signal that may request the transmitting and/or receiving function of the first gateway be activated.

A non-transitory computer readable recording medium may have embodied thereon a computer program for executing the method.

In yet another aspect, a health care system is provided. The health care system includes a sensing unit configured to sense a biological signal of a user, a health care server configured to analyze information regarding health care of the user based on the sensed biological signal, a plurality of gateways configured to receive the biological signal from the sensing unit, transmitting the received biological signal to the health care server, and displaying the information regarding health care, and a health care controller configured to receive the biological signal, configured to determine whether the health care system comprises, in addition to a first gateway through which the sensed biological signal is transmitted and/or received, at least one second gateway through which the sensed biological signal may be transmitted and/or received, configured to determine which gateway the sensed biological signal is to be transmitted and/or received through in response to the health care system comprises the second gateway, and configured to control a transmitting and/or receiving function of each gateway according to a result of the determining. The health care controller may be included in the health care server, the gateways, the sensing unit, or a combination thereof.

In yet another aspect, an apparatus for controlling health care in a health care system is provided. The apparatus includes a communication unit configured to transmit and/or receive a sensed biological signal, a determination unit configured to determine which gateway of a plurality of gateways the sensed biological signal is to be transmitted and/or received through based on a set of predefined conditions, and a communication control unit configured to control a transmitting and/or receiving function of each gateway according to a result of the determining.

Other features and aspects may be apparent from the following detailed description, the drawings, and the claims.

Figure 1:
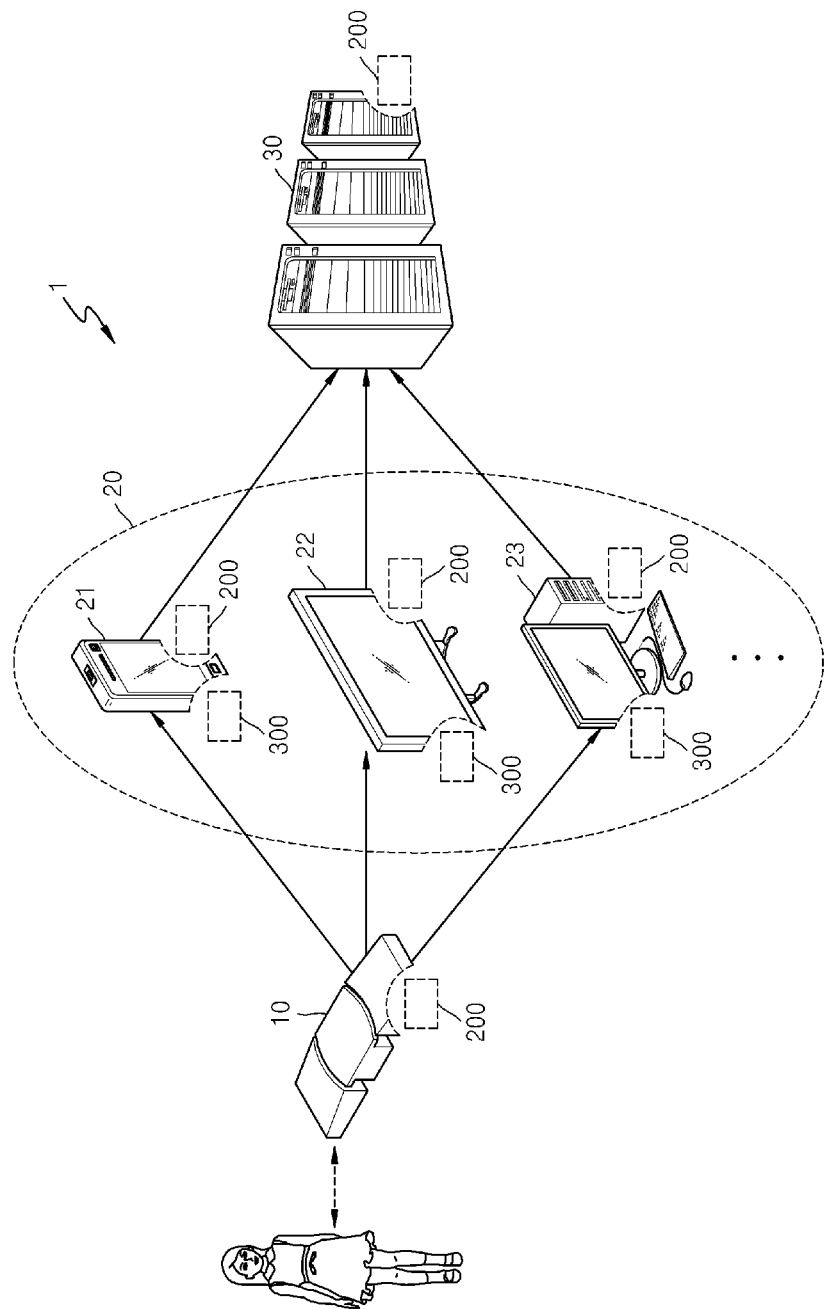
FIG. 1 is a diagram illustrating an example of a health care system.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following description will illustrate examples with reference to the attached drawings.

FIG. 1 illustrates an example of a health care system 1. Referring to FIG. 1, the health care system 1 includes a sensing unit 10, a plurality of gateways 20, and a health care server 30.

Components related to the current example are illustrated in the health care system 1 of FIG. 1. Accordingly, the health care system 1 may also include components other than the components illustrated in FIG. 1.

Referring to FIG. 1, a health care controller 200 includes the sensing unit 10, each gateway 20, the health care server 30, or a combination thereof. Examples for illustrating that providing of health care by the health care system 1 may be differently controlled according to where the health care controller 200 is disposed will be described later.

The health care system 1 provides health care based on a user's biological signal.

The sensing unit 10 senses a user's biological signal. The sensing unit 10 is carried by the user and communicates with other devices in a wired or wireless manner to transmit the sensed biological signal to the other devices. In this regard, the sensing unit 10 includes one or more sensors that may sense, for example, an electrocardiogram (ECG) signal or an electromyogram (EMG) signal. In other words, the sensing unit 10 is not limited to any one device for sensing a biological signal.

In a non-limiting example, in the health care system 1, the sensing unit 10 is carried by a user and senses a biological signal. Since the sensing unit 10 may be any device for sensing a biological signal, for example, an ECG sensor or an EMG sensor, which is understood, a description of the sensing unit 10 is omitted.

The gateways 20 include devices that may communicate with other devices in a wired or wireless manner via a network, for example, a portable terminal 21, a TV 22, and a personal computer (PC) 23. The gateways 20 receive a sensed biological signal from the sensing unit 10 and transmit the received biological signal to the health care server 30 to function as passages of the health care system 1.

Also, the gateways 20 receive information regarding health care from the health care server 30 and display the information regarding health care on a screen included in each gateway 20. The information regarding health care may be information obtained by the health care server 30 analyzing a sensed biological signal. In other words, the gateways 20 are devices for providing health care to a user.

The health care server 30 analyzes a user's health state based on a biological signal transmitted through the gateways 20. For example, in response to the biological signal being the user's ECG signal, the health care server 30 analyzes the ECG signal to determine a state of the user's heart, for example, to determine whether the user has a heart disease such as atrial or ventricular hypertrophy, cardiac infarction, arrhythmia, or pericarditis. In response to the analysis of the biological signal being finished, the health care server 30 sends a result of the analysis to the gateways 20 and the gateways 20 provide the result as health care to the user.

In a conventional health care system using a mobile device such as a mobile phone, the mobile phone functioning as a gateway continuously receives a user's biological signal from a sensor carried by the user and transmits the received biological signal to a health care server to provide health care to the user via the mobile phone. Accordingly, since a communication module included in the mobile phone continuously operates in order to communicate with the sensor, a large amount of power of a battery of the mobile phone is consumed. Thus, time for other functions of the mobile phone, for example, a calling function or a text message sending function, is reduced.

Also, in response to the mobile phone transmitting and/or receiving processed data regarding a biological signal, a large amount of computing resources of the mobile phone is used, and thus resources for other functions of the mobile phone are reduced. For example, in response to continuous real-time monitoring of the biological signal being necessary, the mobile phone should be within such a distance from the sensor that the mobile phone and the sensor are able to communicate with each other, even while a user is at home, in order to prevent data loss.

In the health care system 1 of the current example, in response to there being, in addition to the portable terminal 21, a device capable of functioning as a gateway, for example, consumer electronics such as the TV 22 or the PC 23, around a user, the health care controller 200 controls the TV 22 to function as a gateway and controls the portable terminal 21 to stop functioning as a gateway, thereby decreasing consumption of power and resources of the portable terminal 21. Also, even in response to the user not carrying the portable terminal 21 within a short distance from the sensing unit 10 while the user is at home, the user may be continuously provided health care in real time.

Hereinafter, operations of the health care controller 200 in the health care system 1 will be described. However, the health care controller 200 including components illustrated in FIG. 2 will first be described.

Figure 2:
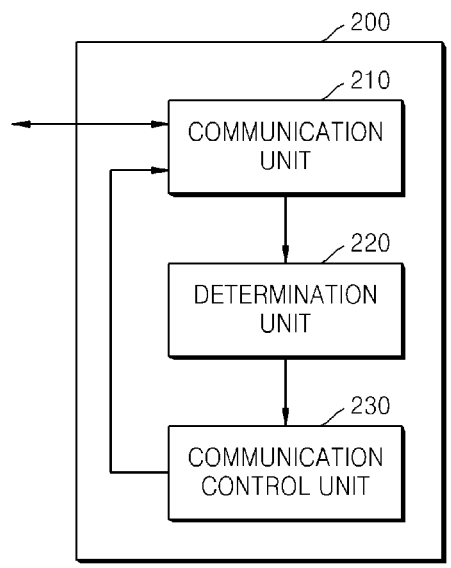
FIG. 2 is a diagram illustrating an example of a health care controller.

FIG. 2 is a diagram illustrating an example of the health care controller 200. Referring to FIG. 2, the health care controller 200 includes a communication unit 210, a determination unit 220, and a communication control unit 230.

The health care controller 200 may include one or more processors. Each processor may be implemented by an array including a plurality of logic gates or by a combination of a general-purpose microprocessor and a memory storing a program executable by the microprocessor. Also, each processor may be implemented by a different type of hardware.

The communication unit 210 transmits and/or receives a user's biological signal sensed by the sensing unit 10 of FIG. 1. In other words, as described above, the communication unit 210 receives the user's biological signal, such as an ECG signal or an EMG signal. As will be described, the communication unit 210 communicates with other devices such as, for example, the portable terminal 21 or the TV 22, in the health care system 1 of FIG. 1 according to where the health care controller 200 is disposed.

The determination unit 220 determines whether the health care system 1 of FIG. 1 includes, in addition to a first gateway through which a biological signal is transmitted and/or received, at least one second gateway through which the biological signal may be transmitted and/or received, and determines which gateway the biological signal is to be transmitted and/or received through in response to the health care system 1 including the second gateway.

For example, in the health care system 1, the determination unit 220 determines whether the TV 22 may transmit and/or receive a biological signal in response to the portable terminal 21 transmitting and/or receiving the biological signal. The determination unit 220 determines, from among the portable terminal 21 and the TV 22, which gateway the biological signal is to be transmitted and/or received through in response to the TV 22 being capable of transmitting and/or receiving the biological signal.

In this regard, in response to the determination unit 220 determining that there is, in addition to a current gateway through which a biological signal is transmitted and/or received, another gateway through which the biological signal may be transmitted and/or received, the determination unit 220 determines which gateway is to transmit and/or receive the biological signal based on a user's setting, processing capacities of the gateways, or a combination thereof. In response to the user previously setting that health care is to be provided through the TV 22 while the user is at home, in response to the user moving from outside of a house to the inside of the house, the determination unit 220 determines that the biological signal is to be transmitted and/or received through the TV 22 instead of the portable terminal 21. Also, the determination unit 220 may determine which gateway is to transmit and/or receive the biological signal based on processing capacities of the portable terminal 21 and the TV 22. In other words, since the processing capacity of the TV 22 is greater than that of the portable terminal 21, in response to the user moving from outside of the house to the inside of the house, the determination unit 220 determines that the biological signal is to be transmitted and/or received through the TV 22 instead of the portable terminal 21.

In response to the determination unit 220 determining that the TV 22 is capable of transmitting and/or receiving a biological signal, the TV 22 transmits and/or receives the biological signal instead of the portable terminal 21, and thus power and resources used by the portable terminal 21 to transmit and/or receive the biological signal are not consumed, as described above.

The communication control unit 230 controls a transmitting and/or receiving function of each gateway according to a result of the determining by the determination unit 220. In other words, in the above-described examples, the communication control unit 230 controls transmitting and/or receiving functions of the portable terminal 21 and the TV 22 according to a result of the determining.

In response to the determination unit 220 determining that the TV 22 is capable of transmitting and/or receiving a biological signal, the communication control unit 230 controls the transmitting and/or receiving function of the portable terminal 21 to be inactive. Thus, power and resources used by the portable terminal 21 to transmit and/or receive the biological signal are not consumed by allowing the transmitting and/or receiving function of the portable terminal 21 to be inactive and allowing the TV 22 to transmit and/or receive the biological signal.

As described above, the health care controller 200 may be included in the sensing unit 10, each gateway 20, the health care server 30 included in the health care system 1, or a combination thereof. Hereinafter, a case where the health care server 30 includes the health care controller 200 will be referred to as a first example, a case where each gateway 20 includes the health care controller 200 will be referred to as a second example, and a case where the sensing unit 10 includes the health care controller 200 will be referred to as a third example.

However, the health care system 1 is not limited thereto. In other words, although the portable terminal 21, the TV 22, and the PC 23 are shown as the gateways 20 of the health care system 1, the health care system 1 may include various different kinds of devices such as, for example, a set top box, a notebook computer, a PC, etc. in addition to the portable terminal 21, the TV 22, and the PC 23 or may include only one kind of device. Even in an environment in which such devices exist, each operation to be described in the follow examples may be expansively applied.

Also, even in response to a user moving from one room to another room while the user is at home, each operation to be described in the follow examples may be expansively applied. In other words, each operation to be described in the follow examples may be expansively applied by assuming that all areas outside a house constitute a first room and all areas inside the house constitute a second room.

First, an operation of the health care system 1 according to the first example is as follows.

Figure 3A:
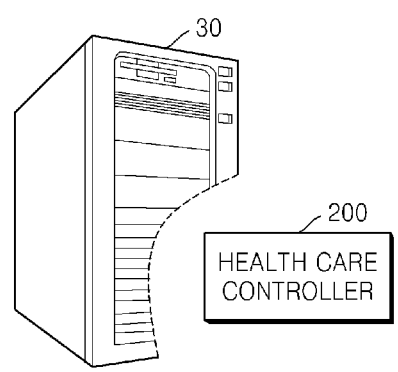
FIG. 3A is a diagram illustrating an example of a health care server.

FIG. 3A illustrate as an example the health care server 30. Referring to FIG. 3A, the health care controller 200 is configured as one module of the health care controller 200.

Figure 3B:
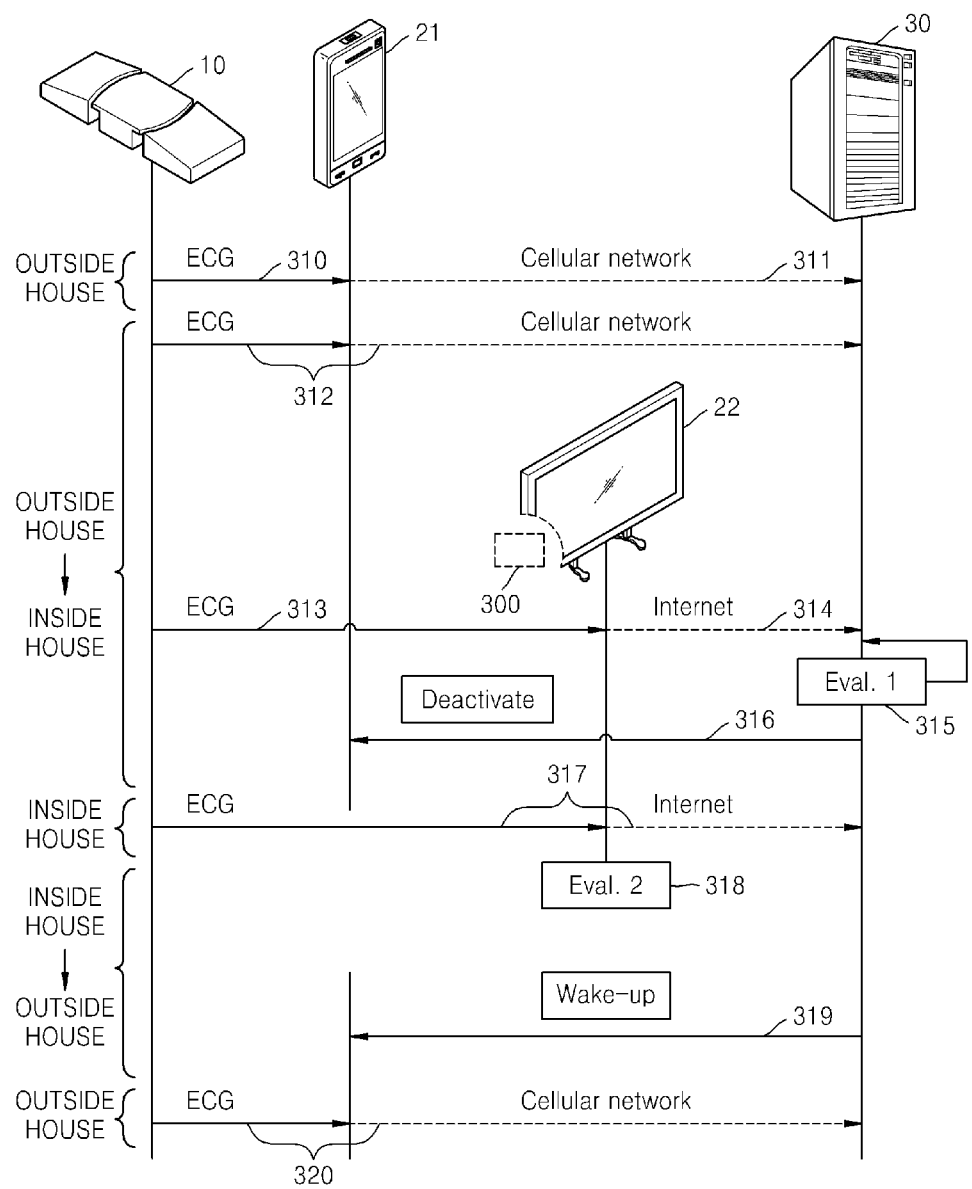
FIG. 3B is a diagram illustrating an example of a method of controlling health care.

FIG. 3B illustrates an example of a method of controlling health care. Referring to FIG. 3B, arrows are illustrated according to time. Operations 310 and 311 illustrate a case where a user stays outside a house, operations 312 through 316 illustrate a case where the user moves from outside the house to inside the house, operation 317 illustrates a case where the user stays inside the house, operations 318 and 319 illustrate a case where the user moves from inside the house to outside the house, and operation 320 illustrates a case where the user stays outside the house.

In operation 310, while the user stays outside the house, the sensing unit 10 transmits a biological signal, for example, an ECG signal, to the portable terminal 21.

In operation 311, the portable terminal 21 receiving the biological signal transmits the biological signal to the health care server 30 via a cellular network. The communication unit 210 of the health care controller 200 included in the health care server 30 receives the biological signal.

In operation 312, even while the user is moving from outside the house to inside the house, the sensing unit 10 transmits the biological signal to the portable terminal 21, and the portable terminal 21 receiving the biological signal transmits the biological signal to the health care server 30 via the cellular network.

In operation 313, also while the user is moving from outside the house to inside the house, the sensing unit 10 transmits the biological signal to the TV 22.

In operation 314, the TV 22 receiving the biological signal transmits the biological signal to the health care server 30 via the Internet in a wired or wireless manner. The communication unit 210 of the health care controller 200 included in the health care server 30 receives the biological signal.

In operation 315, the determination unit 220 1) determines whether the TV 22, in addition to the portable terminal 21, may transmit and/or receive the biological signal and 2) determines, from among the portable terminal 21 and the TV 22, which gateway the biological signal is to be transmitted and/or received through. The determination unit 220 determines whether the biological signal received from the portable terminal 21 is the same as the biological signal received from the TV 22. In response to both the biological signals being the same, according to a result of the determining, the communication control unit 230 generates a deactivation control signal that requests that the transmitting and/or receiving function of the portable terminal 21 be deactivated. Also, in operation 315, the communication control unit 230 may generate a maintaining control signal that maintains that the transmitting and/or receiving function of the TV 22 be maintained.

In operation 316, the communication control unit 230 controls the portable terminal 21 to deactivate the transmitting and/or receiving function of the portable terminal 21 by transmitting the deactivation control signal to the portable terminal 21 via the communication unit 210. Also, in operation 316, the communication control unit 230 may control the TV 22 to maintain the transmitting and/or receiving function of the TV 22 by transmitting the maintaining control signal to the TV 22 via the communication unit 210.

In operation 317, while the user stays inside the house, the sensing unit 10 continuously transmits the biological signal to the TV 22, and the TV 22 receiving the biological signal transmits the biological signal to the health care server 30 via the Internet in a wired or wireless manner. Also, in operation 317, a signal strength measurement unit 300 included in the TV 22 continuously measures a signal strength between the TV 22 and the sensing unit 10.

In operation 318, in response to the signal strength measured by the signal strength measurement unit 300 being less than a threshold value that is previously set or in response to the communication unit 210 not receiving the biological signal from the TV 22, for example, in response to the user moving from inside the house to outside the house, the communication control unit 230 generates a wake-up signal as a control signal that requests that the transmitting and/or receiving function of the portable terminal 21 be activated.

In operation 319, the communication control unit 230 controls the portable terminal 21 by transmitting the wake-up signal to the portable terminal 21 via the communication unit 210.

In operation 320, while the user stays outside the house, the sensing unit 10 transmits the biological signal to the portable terminal 21, and the portable terminal 21 receiving the biological signal transmits the biological signal to the health care server 30 via the cellular network.

Next, an operation of the health care system 1 according to the second example is as follows.

Figure 4A:
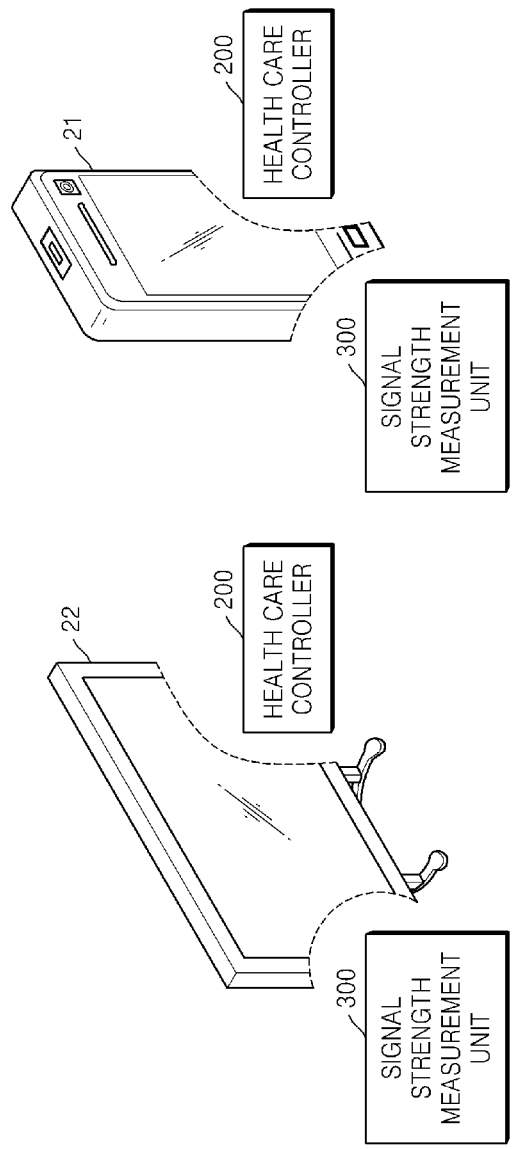
FIG. 4A is a diagram illustrating an example of a portable terminal and a TV.

FIG. 4A illustrates an example of the portable terminal 21. Referring to FIG. 4A, the health care controller 200 is configured as one module of the portable terminal 21 and as one module of the TV 22. The portable terminal 21 and the TV 22 according to the second example may each include the signal strength measurement unit 300.

Figure 4B:
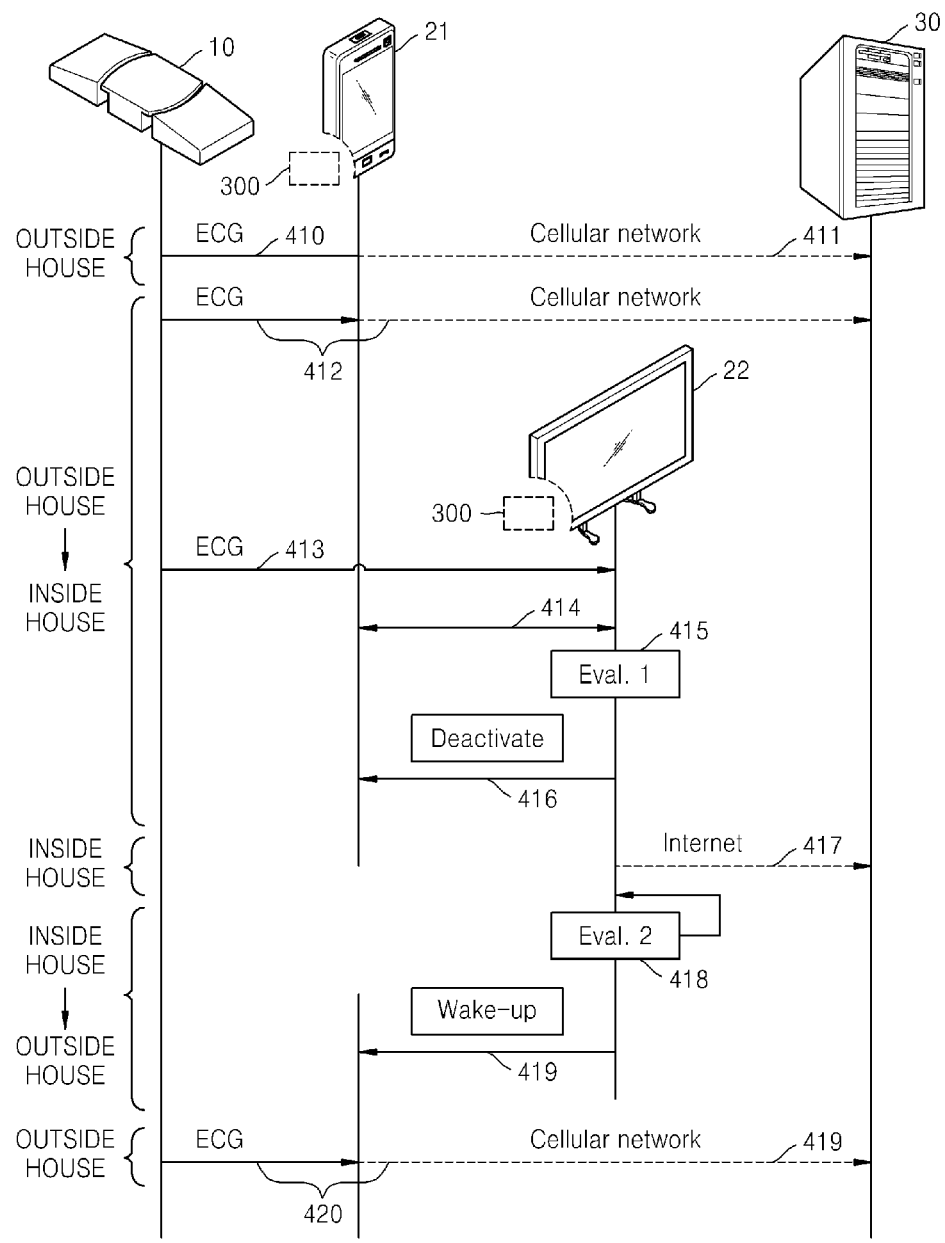
FIG. 4B is a diagram illustrating an example of a method of controlling health care.

FIG. 4B illustrates an example of a method of controlling health care, according to the second example. Referring to FIG. 4B, arrows are illustrated according to time. Operations 410 and 411 illustrate a case where a user stays outside a house, operations 412 through 416 illustrate a case where the user moves from outside the house to inside the house, operation 417 illustrates a case where the user stays inside the house, operations 418 and 419 illustrate a case where the user moves from inside the house to outside the house, and operation 420 illustrates a case where the user stays outside the house.

In operation 410, while the user stays outside the house, the sensing unit 10 transmits a biological signal, for example, an ECG signal, to the portable terminal 21.

In operation 411, the portable terminal 21 receiving the biological signal transmits the biological signal to the health care server 30 via a cellular network. Also, in operation 411, the biological signal is transmitted and/or received based on the communication unit 210 of the health care controller 200 included in the portable terminal 21.

In operation 412, even while the user is moving from outside the house to inside the house, the sensing unit 10 transmits the biological signal to the portable terminal 21, and the portable terminal 21 receiving the biological signal transmits the biological signal to the health care server 30 via the cellular network.

In operation 413, also while the user is moving from outside the house to inside the house, the sensing unit 10 transmits the biological signal to the TV 22.

In operation 414, the communication unit 210 of the portable terminal 21 communicates with the communication unit 210 of the TV 22.

In operation 415, the determination unit 220 included in the portable terminal 21 determines whether the TV 22 may transmit and/or receive the biological signal and determines, from among the portable terminal 21 and the TV 22, which gateway the biological signal is to be transmitted and/or received through. The determination unit 220 included in the TV 22 may also perform the same determining operation performed by the determination unit 220 included in the portable terminal 21.

In operation 416, in response to the determination unit 220 determines that the TV 22 may transmit and/or receive the biological signal, the communication control unit 230 of the TV 22 controls the portable terminal 21 by transmitting a deactivation control signal that requests that the transmitting and/or receiving function of the portable terminal 21 be deactivated to the portable terminal 21. At this time, the communication control unit 230 of the portable terminal 21 deactivates the transmitting and/or receiving function of the portable terminal 21 according to the received deactivation control signal.

In operation 417, while the user stays inside the house, the TV 22 transmits the biological signal via the Internet in a wired or wireless manner. Also, in operation 417, the biological signal is transmitted based on the communication unit 210 of the health care controller 200 included in the TV 22. The biological signal is received by the health care server 30.

In operation 418, in response to a signal strength measured by the signal strength measurement unit 300 being less than a threshold value that is previously set or in response to the biological signal not being transmitted from the communication unit 210 of the TV 22, for example, in response to the user moving from inside the house to outside the house, the communication control unit 230 of the TV 22 generates a wake-up signal as a control signal that requests that the transmitting and/or receiving function of the portable terminal 21 be activated.

In operation 419, the communication control unit 230 of the TV 22 controls the portable terminal 21 by transmitting the wake-up signal to the portable terminal 21 via the communication unit 201 of the TV 22.

In operation 420, while the user stays outside the house, the sensing unit 10 transmits the biological signal to the portable terminal 21, and the portable terminal 21 receiving the biological signal transmits the biological signal to the health care server 30 via the cellular network.

An operation of the health care system 1 according to the third example is as follows.

Figure 5A:
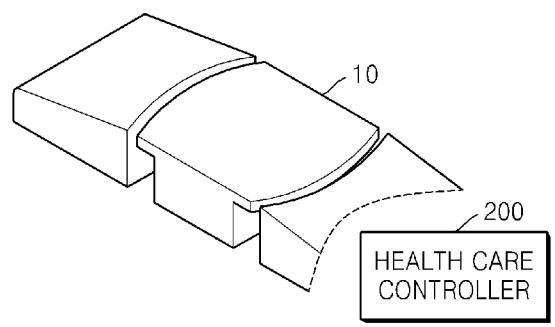
FIG. 5A is a diagram illustrating an example of a sensing unit.

FIG. 5A illustrates an example of the sensing unit 10. Referring to FIG. 5A, the health care controller 200 is configured as one module of the sensing unit 10.

Figure 5B:
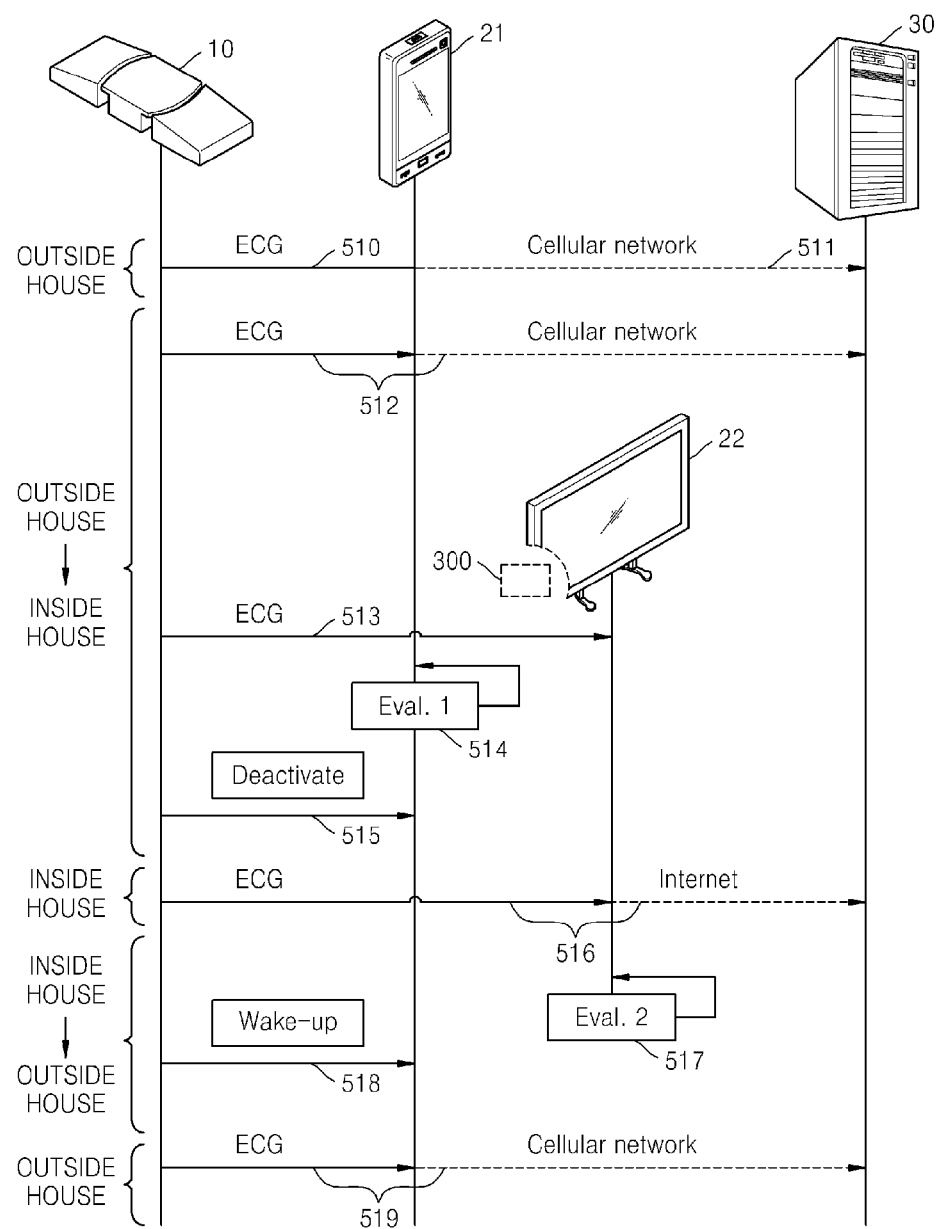
FIG. 5B is a diagram illustrating an example of a method of controlling health care.

FIG. 5B illustrates an example of a method of controlling health care. Referring to FIG. 5B, arrows are illustrated according to time. Operations 510 and 511 illustrate a case where a user stays outside a house, operations 512 through 515 illustrate a case where the user moves from outside the house to inside the house, operation 516 illustrates a case where the user stays inside the house, operations 517 and 518 illustrate a case where the user moves from inside the house to outside the house, and operation 519 illustrates a case where the user stays outside the house.

In operation 510, while the user stays outside the house, the sensing unit 10 transmits a biological signal, for example, an ECG signal, to the portable terminal 21. Also, in operation 510, the biological signal is transmitted based on the communication unit 210 of the health care controller 200 included in the sensing unit 10.

In operation 511, the portable terminal 21 receiving the biological signal transmits the biological signal to the health care server 30 via a cellular network.

In operation 512, even while the user is moving from outside the house to inside the house, the sensing unit 10 transmits the biological signal to the portable terminal 21, and the portable terminal 21 receiving the biological signal transmits the biological signal to the health care server 30 via the cellular network.

In operation 513, also while the user is moving from outside the house to inside the house, the sensing unit 10 transmits the biological signal to the TV 22. Also, in operation 513, the biological signal is transmitted based on the communication unit 210 of the health care controller 200 included in the sensing unit 10.

In operation 514, the determination unit 220 determines whether the TV 22 may transmit and/or receive the biological signal and determines, from among the portable terminal 21 and the TV 22, which gateway the biological signal is to be transmitted and/or received through.

In operation 515, the determination unit 220 determines that the TV 22 may transmit and/or receive the biological signal, and the communication control unit 230 controls the portable terminal 21 by transmitting a deactivation control signal that requests that the transmitting and/or receiving function of the portable terminal 21 be deactivated to the portable terminal 21.

In operation 516, while the user stays inside the house, the sensing unit 10 continuously transmits the biological signal to the TV 22, and the TV 22 receiving the biological signal transmits the biological signal to the health care server 30 via the Internet in a wired or wireless manner. The health care server 30 receives the biological signal.

In operation 517, the signal strength measurement unit 300 included in the TV 22 continuously measures a signal strength between the TV 22 and the sensing unit 10. In response to the signal strength measured by the signal strength measurement unit 300 being less than a threshold value that is previously set or in response to the communication unit 210 not transmitting the biological signal to the TV 22, for example, in response to the user moving from inside the house to outside the house, the communication control unit 230 generates a wake-up signal as a control signal that requests that the transmitting and/or receiving function of the portable terminal 21 be activated and transmits the wake-up signal to the portable terminal 21.

In operation 518, the communication control unit 230 controls the portable terminal 21 by transmitting the wake-up signal to the portable terminal 21.

In operation 519, while the user stays outside the house, the sensing unit 10 transmits the biological signal to the portable terminal 21, and the portable terminal 21 receiving the biological signal transmits the biological signal to the health care server 30 via the cellular network.

As described in the examples of FIGS. 3A through 5B, in the health care system 1, in response to the TV 22 being capable of functioning as a gateway, other than the portable terminal 21, around a user, the health care controller 200 may reduce power and resources consumed by the portable terminal 21 by controlling the TV 22 to function as a gateway and controlling the portable terminal 21 to stop functioning as a gateway. Also, even in response to the user not carrying the portable terminal 21 within a short distance from the sensing unit 10 while the user is at home, the user may be continuously provided health care in real time.

In the examples of FIGS. 3A through 5B, the signal strength measurement unit 300 for measuring a signal strength corresponding to the sensing unit 10 is included in at least one gateway included in the health care system 1. For example, the signal strength measurement unit 300 may be included in the portable terminal 21, the TV 22, and the PC 23 or only in the TV 22.

Figure 6:
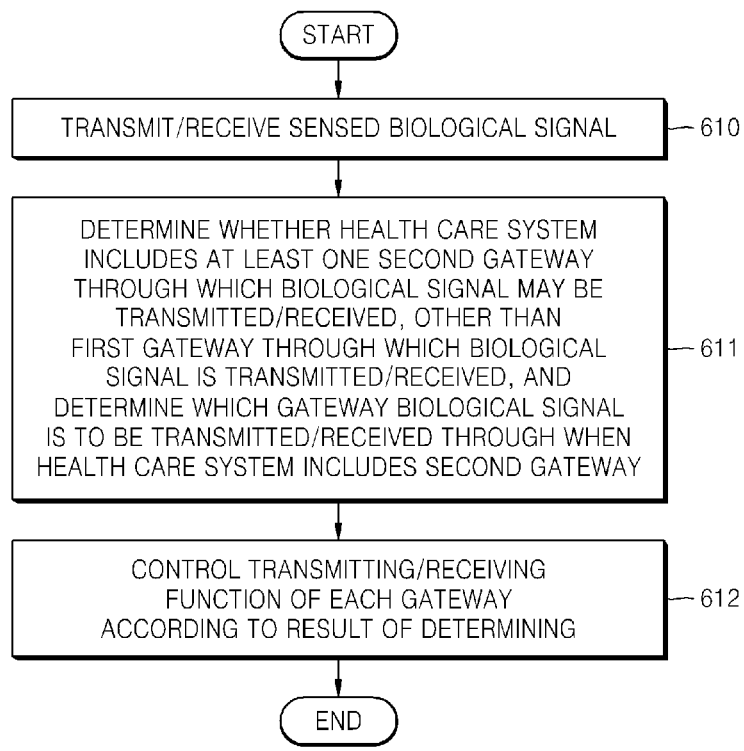
FIG. 6 is a flowchart illustrating an example of a method of controlling health care.

FIG. 6 illustrates an example of a method of controlling health care. Referring to FIG. 6, the method of controlling health care includes the above-described operations performed by the components of the health care controller 1. Accordingly, even though not described below, the description with regard to the health care controller 1 may be applied to the method of controlling health care.

In operation 610, the communication unit 210 transmits and/or receives a biological signal sensed by the sensing unit 10 of FIG. 1. In other words, as described above, the communication unit 210 transmits and/or receives a biological signal such as a user's ECG signal or the user's EMG signal.

In operation 611, the determination unit 220 determines whether the health care system 1 of FIG. 1 includes, in addition to a first gateway through which the biological signal is transmitted and/or received, at least one second gateway through which a biological signal may be transmitted and/or received, and determines which gateway the biological signal is to be transmitted and/or received through in response to the health care system 1 of FIG. 1 includes the second gateway.

In operation 612, the communication control unit 230 controls a transmitting and/or receiving function of each gateway according to a result of the determining.

As described above, in response to a health care system includes a sensor for sensing a user's biological signal, a health care server for analyzing information regarding health care, and a plurality of gateway terminals for delivering the biological signal exist between the sensor and the health care server, biological signal transmitting and/or receiving functions of the gateway terminals may be effectively controlled. Accordingly, each device may be effectively controlled in the health care system so as to reduce loads of devices having a relatively small processing capacity, thereby optimizing operations of the health care system. In other words, a health care system in which different devices are converged to effectively provide health care may be realized.

In particular, in response to a user is provided health care based on a portable terminal outside a house and then moves to inside the house, a home appliance is controlled to newly function as a gateway and the portable terminal is controlled to stop functioning as a gateway, thereby reducing power and resources consumed by the portable terminal. Also, even in response to the user not carrying the portable terminal within a short distance from a sensing unit while the user is at home, the user may be continuously provided health care in real time.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable recording mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described unit to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An apparatus for controlling health care in a health care system, the apparatus comprising:
a communication unit configured to transmit and/or receive a sensed biological signal;
a determination unit configured to determine whether the health care system comprises, in addition to a first gateway through which the sensed biological signal is transmitted and/or received, at least one second gateway through which the sensed biological signal can be transmitted and/or received, and determine which gateway the sensed biological signal is to be transmitted and/or received through in response to the health care system comprising the second gateway; and
a communication control unit configured to control a transmitting and/or receiving function of each gateway according to a result of the determining,
wherein in response to the determination unit determining that the health care system comprises the second gateway, the communication control unit controls the transmitting and/or receiving function of the first gateway to be deactivated.

2. The apparatus of claim 1, wherein in response to the determination unit determining that the health care system comprises the second gateway, the determination unit determines the gateway to transmit and/or receive the sensed biological signal based on a user's setting, processing capacities of the gateways, or a combination thereof.

3. The apparatus of claim 1, wherein at least one of the gateways further comprises a signal strength measurement unit for measuring a signal strength corresponding to a sensing unit for sensing a biological signal.

4. The apparatus of claim 3, wherein the health care controller is comprised in a health care server.

5. The apparatus of claim 4, wherein the determination unit determines whether a biological signal received from the first gateway via the communication unit is the same as a biological signal received from the second gateway, and wherein the communication control unit controls the gateways by generating a control signal for controlling the transmitting and/or receiving function of each gateway according to a result of the determining.

6. The apparatus of claim 5, wherein in response to the determination unit determining that the received biological signals are the same, the communication control unit generates a control signal that requests that the transmitting and/or receiving function of the first gateway be deactivated.

7. The apparatus of claim 5, wherein in response to the measured signal strength is less than a threshold value or in response to the communication unit does not receive a biological signal from the second gateway, the communication control unit generates a control signal that requests the transmitting and/or receiving function of the first gateway be activated.

8. The apparatus of claim 3, wherein the health care controller is comprised in each gateway.

9. The apparatus of claim 8, wherein in response to the determination unit determining that the health care system comprises the second gateway, the communication unit comprised in the second gateway transmits a control signal that requests the transmitting and/or receiving function of the first gateway be deactivated.

10. The apparatus of claim 8, wherein in response to the measured signal strength being less than the threshold value, the communication unit comprised in the second gateway transmits a control signal that requests the transmitting and/or receiving function of the first gateway be activated.

11. The apparatus of claim 3, wherein the health care controller is comprised in the sensing unit.

12. A method of controlling health care in a health care system, the method comprising:
transmitting and/or receiving a sensed biological signal;
determining whether the health care system comprises, in addition to a first gateway through which the sensed biological signal is transmitted and/or received, at least one second gateway through which the sensed biological signal can be transmitted and/or received, and determining which gateway the sensed biological signal is to be transmitted and/or received through in response to the health care system comprising the second gateway; and
controlling a transmitting and/or receiving function of each gateway according to a result of the determining,
wherein in response to a determination determining that the health care system comprises the second gateway, the controlling comprises controlling the transmitting and/or receiving function of the first gateway to be deactivated.

13. The method of claim 12, wherein in response to a determination determining that the health care system comprises the second gateway, the determining comprising determining the gateway to transmit and/or receive the sensed biological signal based on a user's setting, processing capacities of the gateways, or a combination thereof.

14. The method of claim 12, wherein at least one of the gateways measures a signal strength corresponding to a sensing unit for sensing a biological signal.

15. The method of claim 14, wherein a health care controller configured to perform the method of controlling health care is comprised in a health care server, the gateways, the sensing unit, or a combination thereof.

16. The method of claim 15, wherein in response to the health care controller being comprised in the health care server, the determining comprises determining whether a biological signal received from the first gateway is the same as a biological signal received from the second gateway, and the controlling comprises controlling the gateways by generating a control signal for controlling the transmitting and/or receiving function of each gateway according to a result of the determining.

17. The method of claim 16, wherein in response to a determination determining that the received biological signals are the same, the controlling comprises controlling by generating a control signal that requests the transmitting and/or receiving function of the first gateway be deactivated.

18. The method of claim 16, wherein in response to the measured signal strength being less than a threshold value or in response to the health care server not receiving a biological signal from the second gateway, the controlling comprises controlling a control signal that requests the transmitting and/or receiving function of the first gateway be activated.

19. The method of claim 15, wherein in response to the health care controller being comprised in each gateway, in response to a determination determining that the health care system comprises the second gateway, further comprising transmitting a control signal that requests the transmitting and/or receiving function of the first gateway be deactivated.

20. The method of claim 15, wherein in response to the health care controller being comprised in each gateway, in response to the measured signal strength being less than a threshold value, further comprising transmitting a control signal that requests the transmitting and/or receiving function of the first gateway be activated.

21. A non-transitory computer readable recording medium having embodied thereon a computer program for executing the method of claim 12.

22. A health care system comprising:
    a sensing unit configured to sense a biological signal of a user;
    a health care server configured to analyze information regarding health care of the user based on the sensed biological signal;
    a plurality of gateways configured to receive the biological signal from the sensing unit, transmitting the received biological signal to the health care server, and displaying the information regarding health care; and
    a health care controller configured to receive the biological signal, configured to determine whether the health care system comprises, in addition to a first gateway through which the sensed biological signal is transmitted and/or received, at least one second gateway through which the sensed biological signal may be transmitted and/or received, configured to determine which gateway the sensed biological signal is to be transmitted and/or received through in response to the health care system comprises the second gateway, and configured to control a transmitting and/or receiving function of each gateway according to a result of the determining,
    wherein the health care controller is comprised in the health care server, the gateways, the sensing unit, or a combination thereof, and
    wherein in response to a determination determining that the health care system comprises the second gateway, the controlling comprises controlling the transmitting and/or receiving function of the first gateway to be deactivated.

23. An apparatus for controlling health care in a health care system, the apparatus comprising:
    a communication unit configured to transmit and/or receive a sensed biological signal;
    a determination unit configured to determine which gateway of a plurality of gateways the sensed biological signal is to be transmitted and/or received through based on a set of predefined conditions; and
    a communication control unit configured to control a transmitting and/or receiving function of each gateway according to a result of the determining,
    wherein the communication control unit controls the transmitting and/or receiving function of remaining gateways except for the determined gateway to be deactivated.

* * * * *